United States Patent [19]

Ciullo

[11] Patent Number: 4,526,187
[45] Date of Patent: Jul. 2, 1985

[54] AMBULATION AID HAVING BRACKET FOR ATTACHING ACCESSORY MEDICAL DEVICES

[76] Inventor: Jerome V. Ciullo, 2831 Baltane, West Bloomfield, Mich. 48033

[21] Appl. No.: 432,078

[22] Filed: Sep. 30, 1982

[51] Int. Cl.³ .............................................. A61H 3/02
[52] U.S. Cl. ............................. 135/66; 128/DIG. 6; 248/305; 248/311.3
[58] Field of Search ...................... 135/66, 65, 67, 68, 135/69, 70, 71, 72, 73, 74, 75, 76, DIG. 9; 272/70.1, 70.2, 70.3, 70.4; 128/394, DIG. 6, 133; 248/539, 155, 155.1, 155.2, 155.3, 155.4, 155.5, 311.3, 125, 305, 306; D3/7, 8, 9; 24/460, 461, 462, 506, 517, 499, 511

[56] References Cited

U.S. PATENT DOCUMENTS

| | | | |
|---|---|---|---|
| 869,128 | 10/1907 | Autenreith | 135/66 X |
| 1,270,463 | 6/1918 | Tonolli | 135/68 |
| 1,340,014 | 5/1920 | Claflin | 248/305 X |
| 2,244,869 | 6/1941 | Everest et al. | 135/85 X |
| 2,311,049 | 2/1943 | Hedden | 135/68 |
| 2,723,665 | 11/1955 | Goldsmith | 128/DIG. 6 |
| 2,912,991 | 11/1959 | Shinn | 135/66 X |
| 3,318,457 | 5/1967 | Krasnoff | 248/311.3 X |
| 3,771,665 | 11/1973 | Potter | 248/125 X |
| 3,998,418 | 12/1976 | Boulanger | 248/539 X |
| 4,295,483 | 10/1981 | Smith | 135/66 |
| 4,332,378 | 6/1982 | Pryor | 272/70.3 |

FOREIGN PATENT DOCUMENTS

| | | | |
|---|---|---|---|
| 77604 | 8/1919 | Austria | 135/68 |
| 843189 | 6/1970 | Canada | 135/66 |
| 593340 | 10/1947 | United Kingdom | 135/66 |

Primary Examiner—Robert A. Hafer
Assistant Examiner—Arnold W. Kramer
Attorney, Agent, or Firm—Harness, Dickey & Pierce

[57] ABSTRACT

An ambulatory aid takes the form of a crutch having a bracket which includes a generally U-shaped channel for suspending auxilliary medical apparatus, such as IV bottles and the like. A spring loaded strap hingedly connected to the bracket serves to close the U-shaped channel so the medical apparatus will not become unhooked and fall.

18 Claims, 3 Drawing Figures

U.S. Patent    Jul. 2, 1985    4,526,187
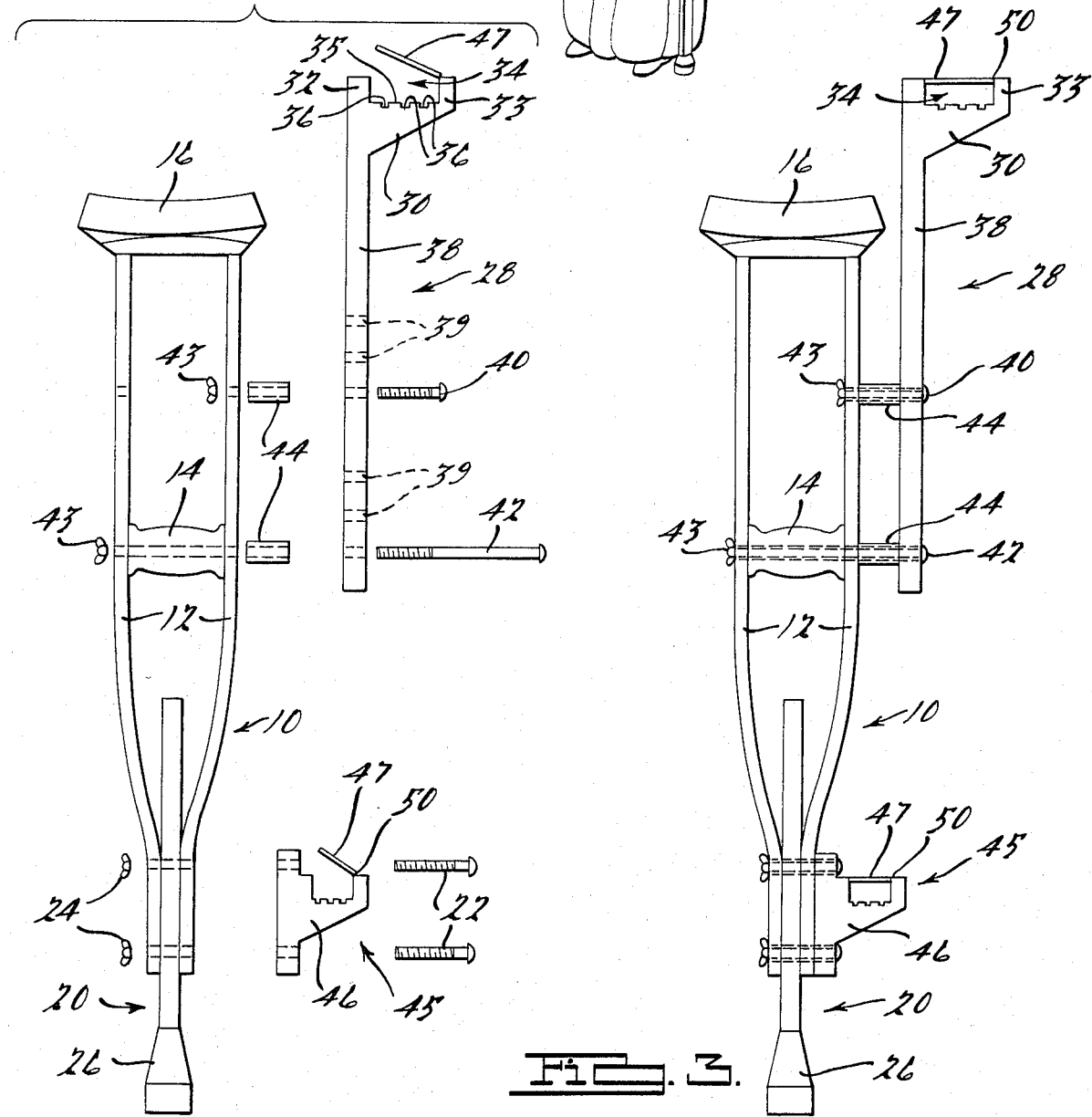

AMBULATION AID HAVING BRACKET FOR ATTACHING ACCESSORY MEDICAL DEVICES

BACKGROUND OF THE INVENTION

This invention pertains generally to ambulatory aids and more particularly to a device attached to a crutch from which medical apparatus, such as containers for intravenous therapy and gravity flow drainage devices, may be suspended.

In the post-operative or in the early post-traumatic period it may often be desirable to have the patient ambulatory as soon as possible. Among the benefits include a shorter post-operative recovery and shorter hospital stay. However, due to the limitations of existing hospital equipment, it is often impracticable for many patients to freely move about.

For example, for patients who must continuously receive intravenous (IV) solutions, present day IV stands are unwieldy castor supported devices which are not easily moved about by the recovering patient. Similarly, patients requiring gravity flow drainage devices, such as hemovac or ready-vac devices, as well as larger devices such as chest tube filter devices may be bed ridden for want of a convenient and safe way of transporting the medical apparatus.

Often, the recoverng patient may require crutches in order to move about. It would therefore be desirable to provide such a patient with a convenient and safe means for transporting the accessory medical apparatus needed for recovery.

SUMMARY OF INVENTION

The present invention comprises an ambulation device or crutch, preferably of the generally Y-shaped type having forked upright members and hand grip disposed between the forked upright members and a padded cross piece under the armpit of the patient. A bracket having a generally downwardly presenting channel is attached to the crutch in a position best suited to the particular medical application. For instance, for IV therapy, the bracket is disposed on an extension or upright arm in order to elevate the IV bottle above the patient's body for proper operation. In the case of a gravity flow drainage device, for example, the bracket is disposed generally beneath the part of the body being drained.

To insure that the medical apparatus will remain safely in place, a closure device, preferably in the form of a spring loaded hinged member, extends across the channel to close it. The invention is readily adaptable to use with existing crutches, such as the Y-shaped crutch. Towards this end the bracket is adapted to be attached to the crutch by means of the same bolts used to attach the hand grip or the adjustable length foot of the crutch.

For a further understanding of the invention and its advantages, references made to the following detailed description together with the accompanying drawings in which:

BRIEF DESCRIPTION OF THE DRAWINGS

FIG. 1 is a perspective view showing the ambulatory device in use.

FIG. 2 is an exploded view illustrating the attachment of the bracket assembly of the invention to a Y-shaped crutch.

FIG. 3 is a similar view illustrating the bracket assembly and crutch combination.

DESCRIPTION OF THE PREFERRED EMBODIMENT

The present invention will be illustrated in conjunction with a generally Y-shaped crutch 10 as this crutch is widely popular. It is to be understood, however, that the invention is not intended to be limited for use only with Y-shaped crutches, as other types of crutches including quad canes or walkers can be similarly used.

The Y-shaped crutch illustrated in the drawings comprises a pair of forked upright members 12, a hand grip 14 disposed between the forked members, and a padded cross piece 16 which is adapted to fit under the armpit of the patient. A foot portion 20, generally comprising the stem of the Y-shaped crutch is adjustably secured to forked upright members 12 as with bolts 22 and wing nuts 24. The foot portion may include a plurality of holes through which bolts 22 may be selectibly inserted, thereby providing a convenient means for lengthening or shortening the crutch. Preferably the foot includes a non-skid grip 26.

A first embodiment of the present invention, useful when it is desired to elevate a piece of medical apparatus above the body, is denoted generally by reference numeral 28. In its presently preferred form, this embodiment comprises an outwardly projecting bracket 30 having a pair of upstanding flanges 32 and 33 which define a generally U-shaped channel 34. The floor 35 of channel 34 is provided with a plurality of grooves 36 which serve to engage and trap the hanging strap or handle of a piece of medical apparatus (not shown). As used herein, this U-shaped channel shall be taken to include not only the generally rectangular U-shape illustrated in the drawings, but also rounded and V-shaped channels as well. The bracket 30 also includes an elongated upright extension 38 which serves to elevate the channel 34 above the padded cross piece 16. Those skilled in the art will appreciate that the particular length selected for extension 38 will depend somewhat on the medical apparatus suspended in the channel 34 or adjusted by alternate holes 39 in strut 38.

The bracket is attached to crutch 10 by any convenient means such as with bolts 40 and 42, and wing nuts 43. If needed, spacers such as tubular spacers 44 may be provided so that the bracket and extension stand outwardly from the forked members 12 a sufficient distance to clear cross piece 16.

In a second embodiment, denoted generally by reference numeral 45, the bracket 46, constructed essentially the same as bracket 30 with upstanding flanges forming a U-shaped channel, is essentially without an extension arm. This embodiment is useful for securing gravity flow drainage devices, chest tube filter devices, and the like, which normally or preferably should be disposed beneath a particular part of the body or at a low center of gravity.

In both embodiments, the bracket includes a closure device which preferably takes the form of a transverse strap or plate 47 hingedly secured to one of the upstanding flanges 32 or 33. The closure device includes a means for locking or biasing the transverse strap or plate across the open channel to insure that devices suspended within the channel do not accidentally become unhooked and fall. Preferably the biasing means takes the form of a spring loaded hinge 50. It will be understood that other types of locking devices may be substituted for the spring loaded hinge transverse strap without departing from the spirit of the invention.

In the case of the Y-shaped crutch, the invention may be advantageously incorporated without making significant structural modifications to the crutch. In view of the fact that most hospitals already maintain a large inventory of such crutches, the ability to this invention without significant modifications of existing crutches is a decided advantage. For example, in order to install the elevated bracket embodiment denoted by reference numeral 28, it is possible to use the same bolt, such as bolt 42, to secure the hand grip 14 as well as the bracket. Similarly, in order to secure the bracket of the second embodiment illustrated generally by reference numeral 45, it is possible to utilize the same bolts, that is bolts 22, to secure the bracket and the foot portion. Thus, in order to add the bracket device to an existing crutch it may be necessary only to furnish slightly longer bolts to accommodate the added thickness of the brackets and possibly to add an additional mounting hole to receive bolt 40 if such is not already conveniently provided.

While the presently preferred embodiments have been illustrated and described in detail, it will be understood that modifications as to details of construction and design are possible without departing from the spirit of the invention or the scope of the following claims.

I claim:

1. A device for attachment to a crutch and from which medical apparatus such as a container for intravenous therapy or a gravity flow drainage device may be suspended, said device comprising upright extension means having an outwardly projecting bracket, said bracket defining a generally U-shaped channel, said channel defining groove means to engage and trap a hanging strap or handle of medical apparatus; movable closure means for bridging the channel to prevent accidental removal of the medical apparatus; and a plurality of spaced attaching means associated with said upright extension means for attaching said device to a crutch, whereby the device can be attached high on a crutch to safely hold medical apparatus such as an intravenous bottle or the like, or low on a crutch to safely hold medical apparatus such as a gravity flow drainage device or the like so that a patient can be ambulatory while utilizing the device with the medical apparatus on a crutch.

2. The device of claim 1 wherein said channel defines a plurality of groove means to engage and trap a hanging strap or handle of medical apparatus.

3. The device of claim 2 wherein said movable closure means is hingedly connected to said bracket and said movable closure means comprises spring means.

4. The device of claim 3 wherein said device is attached to a crutch by attaching means comprising bolt means.

5. The device of claim 1 wherein said movable closure means is hingedly connected to said bracket.

6. The device of claim 1 wherein said movable closure means comprises spring means.

7. The device of claim 1 wherein said attaching means comprises bolt means for securing said device to a crutch.

8. The device of claim 1 wherein said device is attached to a crutch.

9. The device of claim 8 wherein said crutch is a generally Y-shaped crutch having a pair of upright members in forked relationship, a hand grip disposed between said upright members and a cross piece extending between said upright members and adapted to fit under an armpit.

10. The device of claim 9 wherein said attaching means comprises bolt means.

11. The device of claim 10 wherein one of said bolt means also secures said hand grip between said forked upright members.

12. The device of claim 11 wherein said movable closure means is hingedly connected to said bracket.

13. The device of claim 12 wherein said movable closure means comprises spring means.

14. The device of claim 13 wherein said channel defines a plurality of groove means to engage and trap a hanging strap or handle of medical apparatus.

15. The device of claim 10 wherein said crutch includes a downwardly extending member disposed between said upright members and at least one of said bolt means also attaches said upright members to said downwardly extending member.

16. The device of claim 15 wherein said movable closure means is hingedly connected to said bracket.

17. The device of claim 16 wherein said movable closure means comprises spring means.

18. The device of claim 17 wherein said channel defines a plurality of groove means to engage and trap a hanging strap or handle of medical apparatus.

* * * * *